(12) United States Patent
Boehm et al.

(10) Patent No.: US 8,940,901 B2
(45) Date of Patent: Jan. 27, 2015

(54) PROCESS FOR THE PREPARATION OF 3-(6-AMINO-PYRIDIN-3YL)-2-ACRYLIC ACID DERIVATIVES

(71) Applicant: Sanofi, Paris (FR)

(72) Inventors: Claudius Boehm, Frankfurt (DE); Susanne Klein, Frankfurt am Main (DE); Bernd Napierski, Hattersheim (DE); Christian Sommer, Russelsheim (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/889,761

(22) Filed: May 8, 2013

(65) Prior Publication Data

US 2013/0245274 A1 Sep. 19, 2013

Related U.S. Application Data

(63) Continuation of application No. PCT/EP2011/069603, filed on Nov. 8, 2011.

(30) Foreign Application Priority Data

Nov. 11, 2010 (EP) .................................. 10306246

(51) Int. Cl.
| | | |
|---|---|---|
| A61K 31/44 | (2006.01) | |
| C07D 401/00 | (2006.01) | |
| C07D 233/58 | (2006.01) | |
| C07D 233/64 | (2006.01) | |
| C07D 233/84 | (2006.01) | |
| C07D 401/02 | (2006.01) | |

(52) U.S. Cl.
CPC ............ *C07D 233/58* (2013.01); *C07D 233/64* (2013.01); *C07D 233/84* (2013.01); *C07D 401/02* (2013.01)
USPC ....................... 546/275.1; 546/274.4; 514/341

(58) Field of Classification Search
None
See application file for complete search history.

(56) References Cited

U.S. PATENT DOCUMENTS

| | | |
|---|---|---|
| 2002/0183324 A1 | 12/2002 | Jacobson et al. |
| 2003/0083269 A1 | 5/2003 | Brouilette et al. |
| 2003/0199523 A1 | 10/2003 | Snutch |
| 2007/0129341 A1 | 6/2007 | Kallus et al. |
| 2012/0245358 A1 | 9/2012 | Rossen et al. |
| 2013/0012532 A1* | 1/2013 | Nagata et al. ................. 514/275 |

FOREIGN PATENT DOCUMENTS

| | | |
|---|---|---|
| EP | 0405602 | 1/1991 |
| WO | WO 95/35283 | 12/1995 |
| WO | WO 99/30709 | 6/1999 |
| WO | WO 99/36422 | 7/1999 |
| WO | WO 02/00651 | 1/2002 |
| WO | WO 03/013526 | 2/2003 |
| WO | WO 03/061653 | 7/2003 |
| WO | WO 03/091211 | 11/2003 |
| WO | WO 2005/105781 | 11/2005 |
| WO | WO 2010/130718 | 11/2010 |

OTHER PUBLICATIONS

Romo, D. et al. Simultaneous Deprotection and Purification of BOC-amines Based on Ionic Resin Capture. J. Org. Chem. 1998, vol. 63, p. 3471.*
International Search Report for WO2012/062730 dated May 18, 2012.
Xi, et al., Regio-Controlled Synthesis of N-Substituted Immidazoles, Tetrahedron Letters, vol. 46, pp. 7315-7319, (2005).
Barrow, et al., Synthesis and Evaluation of Imidazole Acetic Acid Inhibitors of Activated Thrombin-Activatable Fibrinolysis Inhibitor as Novel Antithrombotics, Journal of Medicinal Chemistry, vol. 46, No. 1, (2003), pp. 5294-5297.
Nantermet, et al., Imidazole Acetic Acid TAFIa Inhibitors: SAR Studies Centered Around the Basic P'1 Group, Bioorganic & Medicinal Chemistry Letters, vol. 14, (2004), pp. 2141-2145.
Bajzar, Thrombin Activatable Fibrinolysis Inhibitor and an Antifibrinolytic Pathway, Arterioscler. Thromb. Vasc. Biol., (2000). vol. 20, pp. 2511-2518.
Bouma, et al., Thrombin-Activatable Fibrinolysis Inhibitor (TAFI, Plasma Procarboxypeptidase B, Procarboxypeptidase R, Procarboxypeptidase U), J. Thrombosis and Haemostasis, 1, (2003), pp. 1566-1574.

(Continued)

*Primary Examiner* — Rita Desai
*Assistant Examiner* — Ben S Michelson
(74) *Attorney, Agent, or Firm* — Kelly L. Bender

(57) ABSTRACT

The present invention relates to a process for the preparation of a compound of the formula I,

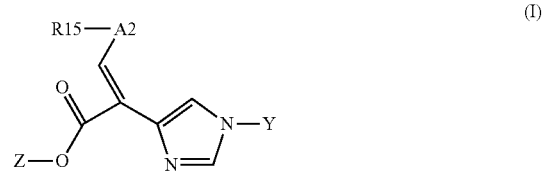

(I)

which comprises reacting a compound of the formula IV

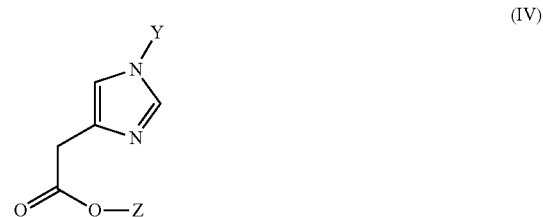

(IV)

with the compound of formula VII R15-A2-CHO and to novel intermediate compounds used therein.

8 Claims, No Drawings

(56) References Cited

OTHER PUBLICATIONS

Marckwald, Ein Beitrag Zur Kenntniss der Imidazole und der Constitution des Glyoxalins, Chem. Ber., (1892), 25, pp. 2354-2373.
Greene, Protection for the Amino Group, Protective Groups in Organic Synthesis, Third Edition, pp. 503-653, (1999).
Jacobson, et al., Basic Principles of Asymmetric Synthesis, Comprehensive Asymmetric Catalysis, pp. 33-97, (1999), Chapter 3.
Tang, et al., New Chiral Phosphorus Ligands for Enantioselective Hydrogenation, Chem. Rev., (2003), vol. 103, pp. 3029-3069.
Satoh, et al., An Efficient Synthesis of a Key Intermediate of DU-6859a Via Asymmetric Microbial Reduction, Chem. Pharm. Bull., vol. 46, No. 4, pp. 587-590, (1998).
Han, et al., Regiospecific Cleavage of Strained tri- and Tetraquinane .beta.-diketones via Retro-Claisen Reaction, Journal of the American Chemical Society, (1982), vol. 104, pp. 318-321.
Wislicenus, Ueber den Benzoylamidooxalessigester (Oxalhippursaureester) und die Benzoylamidobrenztraubensaure, Chem. Ber., (1891), vol. 24, pp. 1257-1263.
Wislicenus, Ueber Oxalessigester, Chem. Ber., (1886), vol. 19, pp. 3225-3228.
English language abstract for WO03/091211 published on Nov. 6, 2003.

\* cited by examiner

PROCESS FOR THE PREPARATION OF 3-(6-AMINO-PYRIDIN-3YL)-2-ACRYLIC ACID DERIVATIVES

This application is a continuation of International Application No. PCT/EP2011/069603, filed Nov. 8, 2011, which is incorporated herein by reference in its entirety; which claims the benefit of priority of European Patent Application No. 10306246.9, filed Nov. 11, 2010.

The present invention relates to a process for the preparation of a compound of the formula I, which can be used in the preparation of compounds which inhibit the enzyme TAFIa (activated thrombin-activatable fibrinolysis inhibitor), and to the novel intermediate compounds used therein.

The enzyme TAFIa is produced for example through thrombin activation from the thrombin-activatable fibrinolysis inhibitor zymogen (TAFI). The enzyme TAFI is also referred to as plasma procarboxypeptidase B, procarboxypeptidase U or procarboxypeptidase R and is a proenzyme similar to carboxypeptidase B (L. Bajzar, Arterioscler. Thromb. Vasc. Biol. 2000, pages 2511-2518).

During formation of a clot, thrombin is generated as the final product of the coagulation cascade and induces conversion of soluble plasma fibrinogen to an insoluble fibrin matrix. At the same time, thrombin activates the endogenous fibrinolysis inhibitor TAFI. Activated TAFI (TAFIa) is thus produced during thrombus formation and lysis from the zymogen TAFI through the action of thrombin; thrombomodulin in a complex with thrombin increases this effect about 1250-fold. TAFIa cleaves basic amino acids at the carboxy end of fibrin fragments. The loss of carboxy-terminal lysines as binding sites for plasminogen then leads to inhibition of fibrinolysis. Efficient inhibitors of TAFIa prevent the loss of these high-affinity lysine binding sites for plasminogen and, in this way, assist endogenous fibrinolysis by plasmin: TAFIa inhibitors have profibrinolytic effects. In order to maintain hemostasis in the blood, mechanisms which lead to the clotting of blood and to the breaking up of clots have developed; these are in equilibrium. If a disturbed equilibrium favors coagulation, fibrin is produced in larger quantities, so that pathological processes of thrombus formation may lead to serious pathological states in humans.

Just like excessive coagulation may lead to serious pathological states caused by thrombosis, an antithrombotic treatment entails the risk of unwanted bleeding through disturbance of the formation of a necessary hemostatic plug. Inhibition of TAFIa increases endogenous fibrinolysis—without influencing coagulation and platelet aggregation—i.e. the disturbed equilibrium is shifted in favor of fibrinolysis. It is thus possible both to counter the buildup of a clinically relevant thrombus, and to increase the lysis of a pre-existing clot. On the other hand, buildup of a hemostatic plug is not impaired, so that a hemorrhagic diathesis is probably not to be expected (Bouma et al., J. Thrombosis and Haemostasis, 1, 2003, pages 1566-1574).

Inhibitors of TAFIa have already been described in the International Applications WO03/013526 and WO2005/105781. A region-specific synthesis of N-substituted imidazoles from α-amino acids is described by Ning Xi et al; Tetrahedron Letters, Vol. 46, No. 43, 2005, pages 7315-7319.

The synthetic routes used to prepare compounds of formula I in the prior art have synthetic strategies with a late introduction of the R1 group. This is shown in Scheme 1 and is highly advantageous for the elucidation of structure-activity-relationships as this strategy allows high diversity at the end of the synthesis. The synthetic routes described are long (7-8 steps) and start from expensive imidazoyl acetic acid 1 towards compound 6 or 7. This strategy necessitates the use of protection and deprotection sequences, thus severely limiting the synthetic efficiency.

Scheme 1

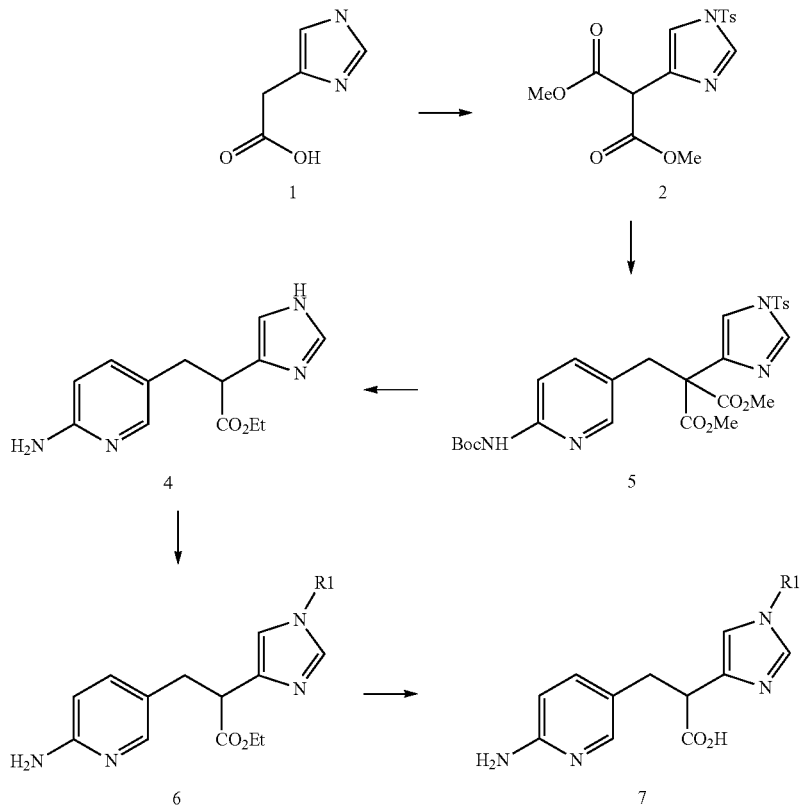

It has now been found that the disadvantages mentioned can be avoided by a short and efficient synthetic route which also dispenses with costly and inconvenient purification steps such as column chromatography.

The object is achieved by using N1-substituted imidazoyl acetic acid derivatives as starting compounds for the synthetic route, which allows the preparation of a compound of formula I in a few chemical reaction steps, in good yields and with high purity.

The invention therefore relates to a process for obtaining the compound of the formula I

R15—A2 (I)

[structure showing R15—A2 connected via C=C to a carbonyl with Z—O and to an imidazole ring with N—Y]

and/or all stereoisomeric forms of the compound of the formula I and/or mixtures of these forms in any ratio, where
A2 is aminopyridyl, in which aminopyridyl is unsubstituted or substituted independently of one another once, twice or three times by halogen or methyl,
Y is —($C_3$-$C_8$)-cycloalkyl, in which cycloalkyl is unsubstituted or substituted independently of one another once, twice or three times by R1,
where R1 is
   a) phenyl, where phenyl is unsubstituted or substituted once, twice or three times independently of one another by —($C_1$-$C_4$) alkyl,
   b) halogen,
   c) —($C_1$-$C_4$)-alkyl,
   d) —($C_3$-$C_6$)-cycloalkyl,
   e) —$CF_3$,
   f) —O—$CF_3$,
   g) triazolyl or
   h) pyridinyl,
R15 is an amino-protecting group and
Z is 1) —($C_1$-$C_6$)-alkyl,
   2) —($C_1$-$C_6$)-alkyl-OH,
   3) —($C_1$-$C_4$)-alkylene-($C_3$-$C_6$)-cycloalkyl,
   4) —$CH_2$-phenyl, wherein phenyl is unsubstituted or substituted once or twice by $NO_2$ or methoxy,
   5) —$CH_2$—CH=$CH_2$ or
   6) —($C_1$-$C_{10}$)-alkylene-O—C(O)—O—($C_3$-$C_6$)-cycloalkyl,
which comprises
A) reacting a compound of the formula IV (IV)

[structure showing imidazole with N—Y and CH2-C(=O)-O—Z substituent]

with the compound of formula VII

R15-A2-CHO (VII)

wherein R15 is an amino-protecting group, to give a compound of formula I, or
B) optionally a compound of the formula I which has been prepared by process step A) and occurs owing to its chemical structure in enantiomeric forms being fractionated by salt formation with enantiopure acids or bases, chromatography on chiral stationary phases or derivatization using chiral enantiopure compounds such as amino acids, separation of the diastereomers obtained in this way, and elimination of the chiral auxiliary groups into the pure enantiomers.

2) The invention also relates to a process for obtaining the compound of the formula I where
A2 is aminopyridyl, in which aminopyridyl is unsubstituted or substituted independently of one another once, twice or three times by halogen or methyl,
Y is —($C_3$-$C_8$)-cycloalkyl, in which cycloalkyl is unsubstituted or substituted independently of one another once, twice or three times by R1,
where R1 is
   a) phenyl, where phenyl is unsubstituted or substituted once, twice or three times independently of one another by —($C_1$-$C_4$) alkyl,
   b) halogen,
   c) —($C_1$-$C_4$)-alkyl,
   d) —($C_3$-$C_6$)-cycloalkyl,
   e) —$CF_3$,
   f) —O—$CF_3$,
   g) triazolyl or
   h) pyridinyl,
R15 is an amino protecting group selected from tert-butyloxycarbonyl, benzyloxycarbonyl, p-methoxybenzylcarbonyl, N-formyl, N-acetyl, N-benzyl, N-1-(diphenyl)methyl, N-trityl, (4-methoxyphenyl)diphenylmethyl, N-dialkyl phosphoramidates and N-p-toluenesulfonyl, and
Z is 1) —($C_1$-$C_6$)-alkyl,
   2) —($C_1$-$C_6$)-alkyl-OH,
   3) —($C_1$-$C_4$)-alkylene-($C_3$-$C_6$)-cycloalkyl or
   4) —($C_1$-$C_{10}$)-alkylene-O—C(O)—O—($C_3$-$C_6$)-cycloalkyl.

3) The invention also relates to a process for obtaining the compound of the formula I where
A2 is 2-aminopyridyl, which is unsubstituted or substituted independently of one another once, twice or three times by F, Cl, Br, I or methyl,
Y is —($C_3$-$C_8$)-cycloalkyl, in which cycloalkyl is unsubstituted or substituted independently of one another once, twice or three times by R1,
where R1 is
   a) phenyl, where phenyl is unsubstituted or substituted once, twice or three times independently of one another by —($C_1$-$C_4$) alkyl,
   b) fluorine,
   c) —($C_1$-$C_4$)-alkyl,
   d) —($C_3$-$C_6$)-cycloalkyl,
   e) —$CF_3$,
   f) —O—$CF_3$,
   g) chlorine,
   h) triazolyl or
   i) pyridinyl,
R15 is tert-butyloxycarbonyl, and
Z is —($C_1$-$C_6$)-alkyl or benzyl.

4) The invention further relates to a process for obtaining the compound of the formula I where
A2 is 2-aminopyridyl,
R15 is tert-butyloxycarbonyl, Y is —($C_3$-$C_8$)-cycloalkyl, which is unsubstituted or substituted by one or two methyl and Z is —($C_1$-$C_4$)-alkyl.

The term "($C_1$-$C_6$)-alkyl" or "($C_1$-$C_{10}$)-alkyl" means hydrocarbon radicals whose carbon chain is straight-chain or branched and comprises 1 to 6 carbon atoms or 1 to 10 carbon atoms, for example methyl, ethyl, propyl, isopropyl, butyl, isobutyl, tertiary butyl, pentyl, isopentyl, neopentyl, hexyl, 2,3-dimethylbutane, neohexyl, heptyl, octanyl, nonanyl or decanyl.

The term "($C_3$-$C_8$)-cycloalkyl" means radicals such as compounds derived from 3- to 8-membered monocycles such as cyclopropyl, cyclobutyl, cyclopentyl, cyclohexyl, cycloheptyl or cyclooctanyl.

The term "CHO" is a formyl residue.

The term "($C_1$-$C_6$)-alkyl-OH" means alcohols such as methanol, ethanol, 1-propanol, isopropanol, 1-butanol, isobutanol, sec-butanol, pentanol or hexanol.

The term "—$CH_2$-phenyl" means benzyl. The term "—$CH_2$—CH=$CH_2$" means allyl. The term "halogen" means fluorine, chlorine, bromine or iodine.

5) A further aspect of the invention relates to compounds of the formula I

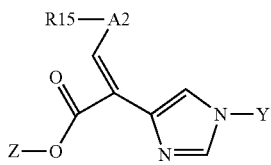

in which

A2 is aminopyridyl, in which aminopyridyl is unsubstituted or substituted independently of one another once, twice or three times by halogen or methyl, Y is —($C_3$-$C_8$)-cycloalkyl, in which cycloalkyl is unsubstituted or substituted independently of one another once, twice or three times by R1, wherein R1 is
  a) phenyl, where phenyl is unsubstituted or substituted once, twice or three times independently of one another by —($C_1$-$C_4$) alkyl,
  b) halogen,
  c) —($C_1$-$C_4$)-alkyl,
  d) —($C_3$-$C_6$)-cycloalkyl,
  e) —$CF_3$,
  f) —O—$CF_3$,
  g) triazolyl or
  h) pyridinyl, R15 is an amino-protecting group and Z is 1) —($C_1$-$C_6$)-alkyl,
  2) —($C_1$-$C_6$)-alkyl-OH,
  3) —($C_1$-$C_4$)-alkylene-($C_3$-$C_6$)-cycloalkyl,
  4) —$CH_2$-phenyl, wherein phenyl is unsubstituted or substituted once or twice by $NO_2$ or methoxy,
  5) —$CH_2$—CH=$CH_2$ or
  6) —($C_1$-$C_{10}$)alkylene-O—C(O)—O—($C_3$-$C_6$)-cycloalkyl.

6) The invention further relates to compounds of the formula I in which

A2 is aminopyridyl, in which aminopyridyl is unsubstituted or substituted independently of one another once, twice or three times by halogen or methyl, Y is —($C_3$-$C_8$)-cycloalkyl, in which cycloalkyl is unsubstituted or substituted independently of one another once, twice or three times by R1, wherein R1 is
  a) phenyl, where phenyl is unsubstituted or substituted once, twice or three times independently of one another by —($C_1$-$C_4$) alkyl,
  b) halogen,
  c) —($C_1$-$C_4$)-alkyl,
  d) —($C_3$-$C_6$)-cycloalkyl,
  e) —$CF_3$,
  f) —O—$CF_3$,
  g) triazolyl or
  h) pyridinyl, R15 is an amino protecting group selected from tert-butyloxycarbonyl, benzyloxycarbonyl, p-methoxybenzylcarbonyl, N-formyl, N-acetyl, N-benzyl, N-1-(diphenyl)methyl, N-trityl, (4-methoxyphenyl)diphenylmethyl, N-dialkyl phosphoramidates and N-p-toluenesulfonyl, and Z is 1) —($C_1$-$C_6$)-alkyl,
  2) —($C_1$-$C_6$)-alkyl-OH,
  3) —($C_1$-$C_4$)-alkylene-($C_3$-$C_6$)-cycloalkyl or
  4) —($C_1$-$C_{10}$)-alkylene-O—C(O)—O—($C_3$-$C_6$)-cycloalkyl.

7) The invention further relates to compounds of the formula I in which

A2 is 2-aminopyridyl, which is unsubstituted or substituted independently of one another once, twice or three times by F, Cl, Br, I or methyl, Y is —($C_3$-$C_8$)-cycloalkyl, which is unsubstituted or substituted by one or two methyl, R15 is tert-butyloxycarbonyl, and Z is —($C_1$-$C_4$)-alkyl or benzyl.

8) The invention further relates to compounds of the formula I in which

A2 is 2-aminopyridyl,

Y is —($C_3$-$C_8$)-cycloalkyl, which is unsubstituted or substituted by one or two methyl, R15 is tert-butyloxycarbonyl, and Z is —($C_1$-$C_4$)-alkyl.

9) The invention further relates to a process for obtaining compounds of the formula II,

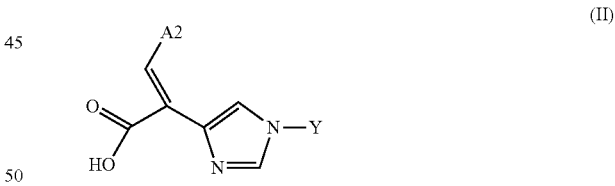

which comprises

C) reacting a compound of the formula I

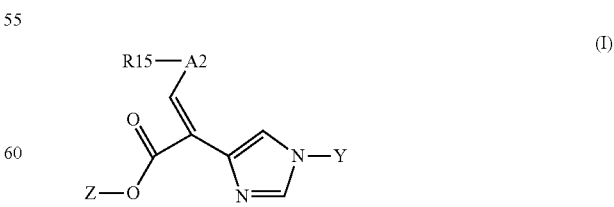

wherein

A2 is aminopyridyl, in which aminopyridyl is unsubstituted or substituted independently of one another once, twice or three times by halogen or methyl, Y is —($C_3$-$C_8$)-cycloalkyl, in which cycloalkyl is unsubstituted or substituted independently of one another once, twice or three times by R1,
where R1 is
  a) phenyl, where phenyl is unsubstituted or substituted once, twice or three times independently of one another by —($C_1$-$C_4$) alkyl,
  b) halogen,
  c) —($C_1$-$C_4$)-alkyl,
  d) —($C_3$-$C_6$)-cycloalkyl,
  e) —$CF_3$,
  f) —O—$CF_3$,
  g) triazolyl or
  h) pyridinyl, and
R15 is an amino protecting group
Z is 1) —($C_1$-$C_6$)-alkyl,
  2) —($C_1$-$C_6$)-alkyl-OH,
  3) —($C_1$-$C_4$)-alkylene-($C_3$-$C_6$)-cycloalkyl,
  4) —$CH_2$-phenyl, wherein phenyl is unsubstituted or substituted once or twice by $NO_2$ or methoxy,
  5) —$CH_2$—CH=$CH_2$ or
  6) —($C_1$-$C_{10}$)-alkylene-O—C(O)—O—($C_3$-$C_6$)-cycloalkyl,
with an acid to give a compound of formula II, or
D) optionally a compound of the formula II which has been prepared by process step C) and occurs owing to its chemical structure in enantiomeric forms being fractionated by salt formation with enantiopure acids or bases, chromatography on chiral stationary phases or derivatization using chiral enantiopure compounds such as amino acids, separation of the diastereomers obtained in this way, and elimination of the chiral auxiliary groups into the pure enantiomers.

Suitable acids are for example mineral acids such as HBr, HCl, HI, $H_2SO_4$, $H_3PO_4$, Organic based acids such as acetic acid, trifluoromethane sulfonic acid or trifluoroacetic acid can also be used, preferred is acetic acid. Solvents used in step C) are ether type solvents such as tetrahydrofuran (THF), dioxane or tert-butyl methyl ether (MTBE), or protic solvents such as water or alcohols.

10) The invention also relates to a process for obtaining the compound of the formula II where
A2 is aminopyridyl, in which aminopyridyl is unsubstituted or substituted independently of one another once, twice or three times by halogen or methyl,
Y is —($C_3$-$C_8$)-cycloalkyl, in which cycloalkyl is unsubstituted or substituted independently of one another once, twice or three times by R1,
where R1 is
  a) phenyl, where phenyl is unsubstituted or substituted once, twice or three times independently of one another by —($C_1$-$C_4$) alkyl,
  b) halogen,
  c) —($C_1$-$C_4$)-alkyl,
  d) —($C_3$-$C_6$)-cycloalkyl,
  e) —$CF_3$,
  f) —O—$CF_3$,
  g) triazolyl or
  h) pyridinyl,
R15 is an amino protecting group selected from tert-butyloxycarbonyl, benzyloxycarbonyl, p-methoxybenzylcarbonyl, N-formyl, N-acetyl, N-benzyl, N-1-(diphenyl)methyl, N-trityl, (4-methoxyphenyl)diphenylmethyl, N-dialkyl phosphoramidates and N-p-toluenesulfonyl, and
Z is 1) —($C_1$-$C_6$)-alkyl,
  2) —($C_1$-$C_6$)-alkyl-OH,
  3) —($C_1$-$C_4$)-alkylene-($C_3$-$C_6$)-cycloalkyl or
  4) —($C_1$-$C_{10}$)-alkylene-O—C(O)—O—($C_3$-$C_6$)-cycloalkyl.

11) The invention also relates to a process for obtaining the compound of the formula II where
A2 is 2-aminopyridyl, which is unsubstituted or substituted independently of one another once, twice or three times by F, Cl, Br, I or methyl,
Y is —($C_3$-$C_8$)-cycloalkyl, in which cycloalkyl is unsubstituted or substituted independently of one another once, twice or three times by R1,
where R1 is
  a) phenyl, where phenyl is unsubstituted or substituted once, twice or three times independently of one another by —($C_1$-$C_4$) alkyl,
  b) fluorine,
  c) —($C_1$-$C_4$)-alkyl,
  d) —($C_3$-$C_6$)-cycloalkyl,
  e) —$CF_3$,
  f) —O—$CF_3$,
  g) chlorine,
  h) triazolyl or
  i) pyridinyl,
R15 is tert-butyloxycarbonyl, and
Z is —($C_1$-$C_6$)-alkyl or benzyl.

12) The invention further relates to a process for obtaining the compound of the formula II where
A2 is 2-aminopyridyl,
R15 is tert-butyloxycarbonyl,
Y is —($C_3$-$C_8$)-cycloalkyl, which is unsubstituted or substituted by one or two methyl and
Z is —($C_1$-$C_4$)-alkyl.

13) A further aspect of the invention relates to compounds of the formula II

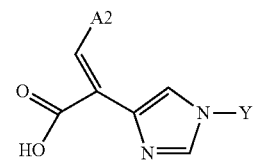

(II)

wherein,
A2 is aminopyridyl, in which aminopyridyl is unsubstituted or substituted independently of one another once, twice or three times by halogen or methyl,
Y is —($C_3$-$C_8$)-cycloalkyl, in which cycloalkyl is unsubstituted or substituted independently of one another once, twice or three times by R1,
wherein R1 is
  a) phenyl, where phenyl is unsubstituted or substituted once, twice or three times independently of one another by —($C_1$-$C_4$) alkyl,
  b) halogen,
  c) —($C_1$-$C_4$)-alkyl,
  d) —($C_3$-$C_6$)-cycloalkyl,
  e) —$CF_3$,
  f) —O—$CF_3$,
  g) triazolyl or
  h) pyridinyl.

14) The invention further relates to compounds of the formula II in which
A2 is aminopyridyl, in which aminopyridyl is unsubstituted or substituted independently of one another once, twice or three times by halogen or methyl, Y is —(C$_3$-C$_8$)-cycloalkyl, in which cycloalkyl is unsubstituted or substituted independently of one another once, twice or three times by R1, wherein R1 is a) phenyl, where phenyl is unsubstituted or substituted once, twice or three times independently of one another by —(C$_1$-C$_4$) alkyl, b) halogen, c) —(C$_1$-C$_4$)-alkyl, d) —(C$_3$-C$_6$)-cycloalkyl, e) —CF$_3$, f) —O—CF$_3$, g) triazolyl or h) pyridinyl.

15) The invention further relates to compounds of the formula II in which

A2 is 2-aminopyridyl, which is unsubstituted or substituted independently of one another once, twice or three times by F, Cl, Br, I or methyl, and Y is —(C$_3$-C$_8$)-cycloalkyl, which is unsubstituted or substituted by one or two methyl.

16) The invention further relates to compounds of the formula II in which

A2 is 2-aminopyridyl, and

Y is —(C$_3$-C$_8$)-cycloalkyl, which is unsubstituted or substituted by one or two methyl.

In the preparation of the compound of the formula I, a procedure is followed in such a manner that, first an imidazoyl acetic ester of formula IV is placed in a solvent and cooled to −70° C. The compound of formula IV is activated with an appropriate base. LiHMDS is preferred. Then an formylpyridin of formula VII is added successively The resultant solution or suspension is stirred under continues cooling at −70° C.

After an appropriate reaction time, the compound of the formula I is precipitated out using a buffer or an acid. The compound of the formula I is isolated, for example, by crystallization or extraction, for example using tetrahydrofuran or tert-butyl methyl ether. Crystallization is promoted by cooling the suspension or further evaporation of the solvents.

Solvents which can be used in this reaction step A) are ethers such as tetrahydrofuran, diethylether, tert-butyl methyl ether, 1,4-dioxan or methyl-tetrahydrofuran. Tetrahydrofuran is preferred.

The temperature used is ranging from 0° C. to −100° C. depending on the boiling point of the solvent.

In the inventive reaction step A) from 10 mol to 200 mol (preferably 96 mol) of the compound of formula VII are used per 100 mol of the compound of formula IV. The amount of solvent used is generally from 5 l to 15 l (preferably 10 l) per kg of the compound of formula IV.

The imidazoyl acetic acid derivatives of formula IV can be prepared by the classical Marckwald synthesis (W. Marckwald, *Chem. Ber.* 1892, 25, 2354, N. Xi et al., *Tetrahedron Lett.* 2005, 46, 7315-7319) as shown in Scheme 2. The γ-amino β-ketoesters (formula III) can be synthesized according to literature (N. Xi et al., *Tetrahedron Lett.* 2005, 46, 7315-7319).

Scheme 2

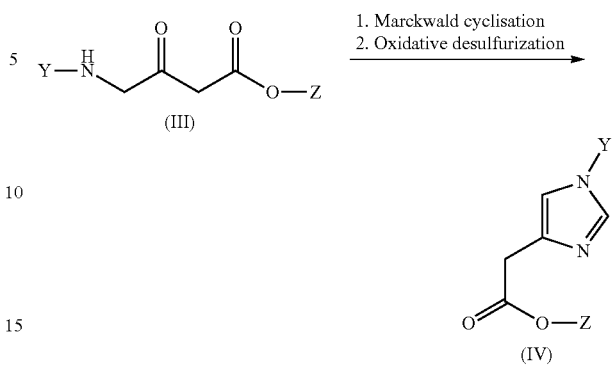

Oxalic diesters are well known in the art and commercially available from multiple vendors (e. g. Sigma-Aldrich Chemie GmbH, Eschenstraβe 5, 82024 Taufkirchen, Germany). One of the oxalic diesters is oxalic acid diethyl ester.

The alkylating agent of formula VII used in process step A) is known in the prior art and can be prepared as described in literature (P. G. Nantermet et al., Bioorg. Med. Chem. Let. 2004, 14, 2141-2145).

R15 is an amino protecting group and can be selected from a variety of groups e.g. listed but not limited to those mentioned in T. W. Greene and P. G. M. Wuts: *Protective Groups in Organic Synthesis*, Third Edition, John Wiley and Sons, New York, 1999, 518-525, 531-540. The amino protecting group chosen is stable under the reaction conditions in process step A) and can be selected e.g. from carbamates, such as tert-butyloxycarbonyl and benzyloxycarbonyl or p-methoxybenzylcarbonyl, amides, such as N-formyl or N-acetyl, N-alkylaryls such as N-benzyl, N-1-(diphenyl)methyl, N-trityl or (4-methoxyphenyl)diphenylmethyl or N—P and N-sulfonyl protecting groups such as N-dialkyl phosphoramidates and N-p-toluenesulfonyl. A specified protecting group is tert-butyloxycarbonyl.

The reaction for process step C), which is the preparation of the compound of formula II, by deprotection of the amino protecting group R15. Deprotection can be performed under standard conditions as described in T. W. Greene and P. G. M. Wuts: *Protective Groups in Organic Synthesis*, Third Edition, John Wiley and Sons, New York, 1999, 518-525, 531-540 and depends on the type of protecting group R15 utilized. If R15 is tert-butoxycarbonyl, deprotection can be performed under acidic conditions. A possible method is acid in a protic solvent. Useful acids are mineral acids such as HBr, HCl, HI, H$_2$SO$_4$, H$_3$PO$_4$, Organic based acids such as acetic acid, trifluoromethane sulfonic acid or trifluoroacetic acid can also be used, preferred is acetic acid. Solvents used in this step are ether type solvents such as THF, dioxane or MTBE, or protic solvents such as water or alcohols. A specified ester Z is ethyl and water is a specified solvent, which can be used in process step C).

The temperature used is ranging from 0° C. to 100° C. depending on the boiling point of the solvent.

In the inventive reaction step C) from 1400 mol to 3000 mol of the acid are used per 100 mol of the compound of formula I. The amount of solvent used is generally from 5 l to 15 l per kg of the compound of formula I.

In process steps B and D), the compound of the formulae I or II is, if it occurs as mixture of diastereomers or enantiomers or results as mixtures thereof, separated into the pure stereoisomers either by chromatography on an optionally chiral support material or, if the racemic compound of the formulae I or II are able to form salts, by fractional crystallization of the diastereomeric salts formed with an optically active base or acid as aid. Chiral stationary phases suitable for thin-layer or column chromatography to separate enantiomers are, for example, modified silica gel supports (so-called Pirkle phases) and high molecular weight carbohydrates such as triacetylcellulose. It is also possible to use for analytical purposes gas chromatographic methods on chiral stationary phases after appropriate derivatization known to the skilled worker. To separate enantiomers of the racemic carboxylic acids, diastereomeric salts differing in solubility are formed using an optically active, usually commercially available, base such as (−)-nicotine, (+)- and (−)-phenylethylamine, quinine bases, L-lysine or L- and D-arginine, the less soluble component is isolated as solid, the more soluble diastereomer is deposited from the mother liquor, and the pure enantiomers are obtained from the diastereomeric salts obtained in this way. It is also possible to use enzymes, such as esterases, in the in the resolution of racemic mixtures to the pure enantiomers. It is further possible in the same way in principle to convert the racemic compounds of the formula I containing a basic group such as an amino group with optically active acids such as (+)-camphor-10-sulfonic acid, D- and L-tartaric acid, D- and L-lactic acid and (+) and (−)-mandelic acid into the pure enantiomers. Chiral compounds containing alcohol or amine functions can also be converted with appropriately activated or, where appropriate, N-protected enantiopure amino acids into the corresponding esters or amides, or conversely chiral carboxylic acids can be converted with carboxyl-protected enantiopure amino acids into the amides or with enantiopure hydroxy carboxylic acids such as lactic acid into the corresponding chiral esters. The chirality of the amino acid or alcohol residue introduced in enantiopure form can then be utilized for separating the isomers by carrying out a separation of the diastereomers which are now present by crystallization or chromatography on suitable stationary phases and then eliminating the included chiral moiety by suitable methods.

A further possibility with some of the compounds of the invention is to employ diastereomerically or enantiomerically pure starting materials to prepare the framework structures. It is thus possible where appropriate also to employ other or simplified processes for purifying the final products.

17) The invention further relates to a process for obtaining compounds of the formula V,

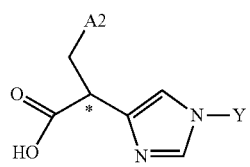

(V)

wherein

A2 is aminopyridyl, in which aminopyridyl is unsubstituted or substituted independently of one another once, twice or three times by halogen or methyl, Y is —($C_3$-$C_8$)-cycloalkyl, in which cycloalkyl is unsubstituted or substituted independently of one another once, twice or three times by R1, where R1 is
a) phenyl, where phenyl is unsubstituted or substituted once, twice or three times independently of one another by —($C_1$-$C_4$) alkyl,
b) halogen,
c) —($C_1$-$C_4$)-alkyl,
d) —($C_3$-$C_6$)-cycloalkyl,
e) —$CF_3$,
f) —O—$CF_3$,
g) triazolyl or
h) pyridinyl, which comprises E) reacting a compound of the formula IV

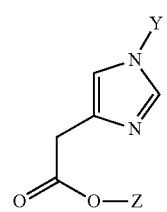

(IV)

wherein
Z is 1) —($C_1$-$C_6$)-alkyl,
2) —($C_1$-$C_6$)-alkyl-OH,
3) —($C_1$-$C_4$)-alkylene-($C_3$-$C_6$)-cycloalkyl,
4) —$CH_2$-phenyl, wherein phenyl is unsubstituted or substituted once or twice by $NO_2$ or methoxy,
5) —$CH_2$—CH=$CH_2$ or
6) —($C_1$-$C_{10}$)-alkylene-O—C(O)—O—($C_3$-$C_6$)-cycloalkyl,
and Y is as defined above,
with the compound of formula VII

R15-A2-CHO   (VII)

wherein R15 is an amino-protecting group and A2 is as defined above, to give a compound of formula I,

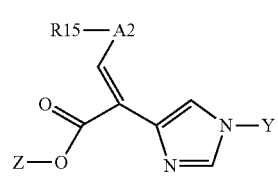

(I)

F) reacting a compound of the formula I with an acid to give a compound of formula II,

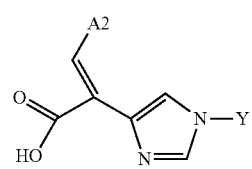

(II)

G) and hydrogenating a compound of the formula II, wherein the compound of formula II may be present in the E or in the Z configuration on the double bond, in the presence of hydrogen and a catalyst to give a compound of formula V, wherein the compound of formula V is present either as the R- or S-enantiomer or as an enantiomer mixture in which one enantiomer is enriched compared to the other.

The term "catalyst" refers to compounds as described, for example, by E. N. Jacobson, A. Pfaltz, H. Yamamoto in *Comprehensive Asymmetric Catalysis*, Springer-Verlag, 1999 or X. Zhang, *Chemical Reviews*, 2003, 103, 3029-3069 and the literature cited therein, for example optically active rhodium, ruthenium or iridium complexes or mixtures thereof. The catalytically active complex is formed by reaction of a metal complex with an optically active phosphine or amine.

The asterisk on a carbon atom in the compound of the formula V means that the particular carbon atom is chiral and that the compound is present either as the R- or S-enantiomer or as an enantiomer mixture in which one enantiomer is enriched compared to the other.

The asymmetric hydrogenation of the compounds of the formula II is advantageously performed at a temperature of from 10° C. to 200° C. and a hydrogen pressure of from 1 bar to 200 bar. The molar catalyst-reactant ratio is advantageously from 1:100 to 1:10 000.

Suitable solvents for the asymmetric hydrogenation are, for example, water, lower alcohols such as methanol, ethanol, trifluoroethanol, propanol or isopropanol, aromatic hydrocarbons such as toluene, ketones such as acetone, halogenated hydrocarbons such as dichloromethane, carboxylic esters such as ethyl acetate, and ethers such as tetrahydrofuran or a mixture of solvents. Suitable additives for the asymmetric hydrogenation are, e.g. sodiummethoxide, trifluoromethansulfonic acid or triethylamine. Enantiomer mixtures should be understood here to mean in particular those in which one enantiomer is enriched compared to the other.

Preferred is an asymmetric hydrogenation.

It is possible that the sequence of the reactions steps might vary.

In the preparation of the compound of the formula IV, a procedure is followed in such a manner that, first an α-aminocarbonyl compound of formula III or a salt thereof is placed in a solvent mixture of water and an alcohol and a thiocyanate salt such as KSCN or NaSCN is added successively. The resultant solution or suspension is heated. After an appropriate reaction time the mixture is cooled to room temperature and the compound of formula IV is extracted or crystallized from the aqueous phase. Extraction can be performed by ethyl acetate. Crystallization is promoted by cooling the suspension or further evaporation of the solvents.

Solvents which can be used in said reaction are alcohols such as methanol, ethanol, propanol, isopropanol, tert.-butanol or butanol. tert.-Butanol is preferred.

The temperature used is ranging from 0° C. to 100° C. depending on the boiling point of the solvent.

The compound of formula III can be prepared by methods known from the literature such as described in K. Satoh et al., *Chem. Pharm. Bull.* 1998, 46, 587.

The invention is illustrated in detail below with reference to examples.

End products are determined generally by $^1$H NMR (400 MHz, in $CDCl_3$ or DMSO-$d_6$).

Temperature data are in degrees Celsius, RT means room temperature (22° C. to 26° C.), min means minute. $t_R$ means retention time.

TFA means trifluoroacetic acid
MeCN means acetonitrile.
AcOEt means Ethyl Acetate
MTBE means Methyl t-Butyl Ether
TMEDA means N,N,N',N'-Tetramethylethylenediamine
cataCXium® A means Butyldi-1-adamantylphosphine
Pd(OAc)$_2$ means Palladium(II) acetate
LiHMDS means Lithium Hexamethyldisilazide
TFE means Trifluoroethanol
ACN means Acetonitrile
TEA means Triethylamine
AcetAc means Acetoacetate Abbreviations used are either explained or correspond to the customary conventions.

EXAMPLE 1

(1-Cyclohexyl-1H-imidazol-4-yl)-acetic acid ethyl ester 200 g (0.758 mol) 4-Cyclohexylamino-3-oxo-butyric acid ethyl ester hydrochloride were dissolved in 360 ml water and 120 ml tert-butanol and were heated to 90° C. Then 88.4 g (0.91 mol) KSCN were added and the mixture was heated for 20 s, thereby a phase separation occurred. After cooling to RT, the phases were separated and the aqueous layer was extracted with AcOEt. The combined organic layers were washed with Brine, dried with $MgSO_4$ and concentrated. The solid was digested in MTBE and filtered to yield 192 g (0.715 mol, 94%) of (1-Cyclohexyl-2-thioxo-2,3-dihydro-1H-imidazol-4-yl)-acetic acid ethyl ester as a beige solid. HPLC: $t_R$=1.16 min (YMC J' sphere ODS H 80 20×2.1 mm, 4 µm, A: $H_2O$+0.05% TFA, B: MeCN, 4%→95% B in 2 min, 1 ml/min, 30° C.); Mass (ES+) ($C_{13}H_{20}N_2O_2S$): calculated. 268. found 269 [M+H]$^+$.

80.0 g (0.298 mol) of (1-Cyclohexyl-2-thioxo-2,3-dihydro-1H-imidazol-4-yl)-acetic acid ethyl ester, dissolved in 200 ml acetic acid, were slowly added to $H_2O_2$ in 400 ml acetic acid at 0° C. within 90 min at 10° C. After addition the cooling was removed and the mixture was allowed stirring for 1 h. The solution was carefully poured into 80 g $Na_2SO_3$ in 300 ml water and ice. The slurry was concentrated and the acidic residue was treated with saturated aqueous $K_2CO_3$ and saturated aqueous $NaHCO_3$ (pH 8). The mixture was extracted with AcOEt (1×400 ml, 2×150 ml). The combined organic layers were washed with brine, dried with $MgSO_4$, concentrated and dried under reduced pressure and gave 70.0 g (0.296 mmol, 99%) of (1-Cyclohexyl-1H-imidazol-4-yl)-acetic acid ethyl ester as a brown oil which could be used without further purification in step A of Example 1.

HPLC: $t_R$=0.77 min (YMC J' sphere ODS H 80 20×2.1 mm, 4 µm, A: $H_2O$+0.05% TFA, B: MeCN, 4%→95% B in 2 min, 1 ml/min, 30° C.);

Mass (ES+) ($C_{13}H_{20}N_2O_2$): calculated. 236. found 237 [M+H]$^+$,

EXAMPLE 2

(5-Formyl-pyridin-2-yl)-carbamic acid tert-butyl ester 6.0 g (21.3 mmol) of (5-Bromo-pyridin-2-yl)-carbamic acid tert-butyl ester was dissolved in THF (55 mL). A solution of 4.9 mL (32 mmol) TMEDA, 241 mg (0.64 mmol) CataCxium A, and 48 mg (0.213 mmol) Pd(OAc)$_2$ in THF (5 mL) was added and the mixture was treated with 5 bar synthesis gas at 100° C. for 16 h.

After cooling, the salts were filter off and the mixture was poured onto water (200 mL). The precipitated was filtered and rinsed with additional water to yield 4.8 g (quant.) HPLC: $t_R$=1.2 min (YMC J'sphere ODS H 80 20×2.1 mm, 4 µm, A: $H_2O$+0.05% TFA, B: MeCN, 4%-95% in 2.45 min, 1 mL/min, 30° C.

EXAMPLE 3

(E)-3-(6-tert-Butoxycarbonylamino-pyridin-3-yl)-2-(1-cyclohexyl-1H-imidazol-4-yl)-acrylic acid ethyl ester (Z)-3-(6-tert-Butoxycarbonylamino-pyridin-3-yl)-2-(1-cyclohexyl-1H-imidazol-4-yl)-acrylic acid ethyl ester A solution of LiHMDS in THF (246 mL, 261.0 mmol) was cooled to −70° C. 22.7 g (96.0 mmol) of the compound according to Example 1 dissolved in THF (80 mL) was added drop wise to this solution and stirred for additional 20 minutes at −20° C. The mixture was re-cooled to −70° C. and a solution of 20.5 g (92.3 mmoL) of the compound according to Example 2 in THF (300 mL) was added dropwise. Stirring was continued at −70° C. until complete conversion was achieved. The mixture was warmed to −20° C. and 12.7 mL (91.5 mmol) triethylamine and 21.1 mL (271.0 mmol) methansulfonic acid chloride were added. The mixture was allowed to warm to ambient temperature and stirring was continued until conversion was complete. MTBE (400 mL) and water (400 mL) were added and phases were separated. The organic layer was washed with brine (400 mL). The solvent was evaporated to yield the product (42 g) as a mixture of E/Z-isomeres. The crude product was used as is in the next step.

HPLC: $t_R$=1.15 and 1.20 min (YMC J'sphere ODS H 80 20×2.1 mm, 4 µm, A: $H_2O$+0.05% TFA, B: MeCN, 4%-95% in 2.45 min, 1 mL/min, 30° C.

EXAMPLE 4

(E)-3-(6-Amino-pyridin-3-yl)-2-(1-cyclohexyl-1H-imidazol-4-yl)-acrylic acid (Z)-3-(6-Amino-pyridin-3-yl)-2-(1-cyclohexyl-1H-imidazol-4-yl)-acrylic acid 100 g crude acrylic acid ester isomeric mixture prepared according to Example 3 was dissolved in 1 L HCl (5 N) and heated to reflux until complete conversion was achieved. The mixture was cooled to ambient temperature and the pH was adjusted to 7 with concentrated NaOH. The precipitate was filtered off and crystallized from boiling water to yield 25.2 g of (E)-3-(6-Amino-pyridin-3-yl)-2-(1-cyclohexyl-1H-imidazol-4-yl)-acrylic acid.

$^1$H-NMR (600.2 MHz, $CD_4OD$):=1.34 (m, 2H), 1.52 (m, 2H), 1.77 (m, 4H), 1.94 (m, 2H), 2.18 (m, 2H), 4.22 (dddd, J=1.52, 1.77, 7.42, 8.44, 1H), 6.51 (d, J=7.86 Hz, 1H), 7.19 (d, J=7.82 Hz, 1H), 7.41 (dd, J=4.22, 8.44 Hz, 1H), 7.82 (dd, J=7.19, 7.86 Hz, 1H), 7.86 (dd, J=7.19, 7.82 Hz, 1H), 8.44 (dd, J=4.22, 7.42 Hz, 1H).

HPLC: $t_R$=3.60 (Z) and 3.95 (E) min (YMC_C18 150×4.6 mm, 3 µm, A: 9$H_2O$+1 ACN/0.1 TEA/pH6.5 AcetAc, B: 1$H_2O$+9 ACN/0.1 TEA/pH6.5 AcetAc, 0.8 mL/min, 20° C.

EXAMPLE 5

Preparation of (R)-3-(6-amino-pyridin-3-yl)-2-(1-cyclohexyl-1H-imidazol-4-yl)-propionic acid 10 g (32.01 mmol) of (E)-3-(6-Amino-pyridin-3-yl)-2-(1-cyclohexyl-1H-imidazol-4-yl)-acrylic acid was dissolved in 150 ml in trifluoroethanol (TFE) and 11.34 mL of natriummethoxid solution (4.8 M in methanol) was added. The solution was filtered and the filter was washed with additional 50 ml TFE. The received solutions were combined and de-gased three times.

With exclusion of oxygen an ampoule was charged with 59.86 mg (0.16 mmol) of bis(norbornadiene)Rhodium(I) tetra-fluoroborate and 131.27 mg (0.18 mmol) of Chenphos ($C_{42}H_{53}Fe_2NP_2$) and was dissolved in 10 mL de-gased TFE. The received catalyst solution was mixed with the prepared educt-solution. With exclusion of oxygen, an autoclave was charged with said received mixture. The mixture was hydrogenated under stirring in an autoclave at 40° C. and 80 bar of hydrogen pressure for 24 h. The autoclave was decompressed and purged with nitrogen. The conversion of the hydrogenation was determined by HPLC.

HPLC: $t_R$=5.40 ((E)-3-(6-Amino-pyridin-3-yl)-2-(1-cyclohexyl-1H-imidazol-4-yl)-acrylic acid) and 5.86 ((R)-3-(6-amino-pyridin-3-yl)-2-(1-cyclohexyl-1H-imidazol-4-yl)-propionic acid) min; (YMC-Pack PRO C18RS 150×4.6 mm, 3 µm, Eluent A: 0.8 g ammonium-acetate+1000 mL $H_2O$, Eluent B: Methanol; Flow: 0.8 mL/min, 30° C. Yield: 99.35%.

The enantioselectivity was determined by HPLC on chiral phase; Eluent: (0.5 g ammoniumacetate in 500 ml $H_2O$)/ACN (1:1), Column: Chirobiotic R; 250×4.6 mm; 5 µm; Flow: 1.0 mL/min; 45° C.; enantiomer purity grade ee: 95.5%

What is claimed is:
1. A process for obtaining the compound of the formula I:

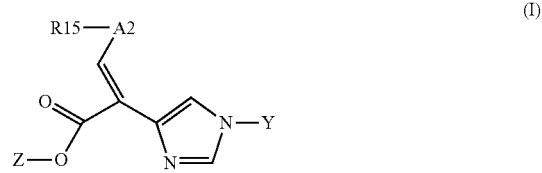

or a stereoisomeric form of the compound of the formula I or a mixture of any stereoisomeric forms of the compound of the formula I in any ratio, wherein A2 is aminopyridyl, in which aminopyridyl is unsubstituted or substituted independently of one another once, twice or three times by halogen or methyl;

Y is —($C_3$-$C_8$)-cycloalkyl, in which cycloalkyl is unsubstituted or substituted independently of one another once, twice or three times by R1,
  wherein R1 is
    a) phenyl, where phenyl is unsubstituted or substituted once, twice or three times independently of one another by —($C_1$-$C_4$) alkyl,
    b) halogen,
    c) —($C_1$-$C_4$)-alkyl,
    d) —($C_3$-$C_6$)-cycloalkyl,
    e) —$CF_3$,
    f) —O—$CF_3$,
    g) triazolyl or
    h) pyridinyl;

R15 is an amino-protecting group; and

Z is 1) —($C_1$-$C_6$)-alkyl,
  2) —($C_1$-$C_6$)-alkyl-OH,
  3) —($C_1$-$C_4$)-alkylene-($C_3$-$C_6$)-cycloalkyl,
  4) —$CH_2$-phenyl, wherein phenyl is unsubstituted or substituted once or twice by $NO_2$ or methoxy,
  5) —$CH_2$—CH═$CH_2$ or
  6) —($C_1$-$C_{10}$)-alkylene-O—C(O)—O—($C_3$-$C_6$)-cycloalkyl;

which process comprises

A) reacting a compound of the formula IV:

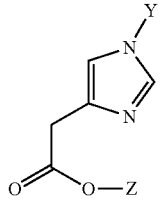
(IV)

with the compound of formula VII:

R15-A2-CHO    (VII)

wherein R15 is an amino-protecting group, to give a compound of formula I, and

B) optionally, when the compound of the formula I prepared by process step A) is in enantiomeric forms, fractionating by salt formation with enantiopure acids or bases; or performing chromatography on chiral stationary phases; or derivatizing using chiral enantiopure compounds, separating the diastereomers obtained in this way, and eliminating the chiral auxiliary groups to obtain pure enantiomers.

2. The process as claimed in claim 1, wherein the compound of formula I is prepared where A2 is aminopyridyl, in which aminopyridyl is unsubstituted or substituted independently of one another once, twice or three times by halogen or methyl;

Y is —$(C_3$-$C_8)$-cycloalkyl, in which cycloalkyl is unsubstituted or substituted independently of one another once, twice or three times by R1, where R1 is
a) phenyl, where phenyl is unsubstituted or substituted once, twice or three times independently of one another by —$(C_1$-$C_4)$ alkyl,
b) halogen,
c) —$(C_1$-$C_4)$-alkyl,
d) —$(C_3$-$C_6)$-cycloalkyl,
e) —$CF_3$,
f) —O—$CF_3$,
g) triazolyl or
h) pyridinyl;

R15 is an amino protecting group selected from tert-butyloxycarbonyl, benzyloxycarbonyl, p-methoxybenzylcarbonyl, N-formyl, N-acetyl, N-benzyl, N-1-(diphenyl)methyl, N-trityl, (4-methoxyphenyl)diphenylmethyl, N-dialkyl phosphoramidates and N-p-toluenesulfonyl; and Z is 1) —$(C_1$-$C_6)$-alkyl,
2) —$(C_1$-$C_6)$-alkyl-OH,
3) —$(C_1$-$C_4)$-alkylene-$(C_3$-$C_6)$-cycloalkyl or
4) —$(C_1$-$C_{10})$-alkylene-O—C(O)—O—$(C_3$-$C_6)$-cycloalkyl.

3. The process as claimed in claim 1, wherein the compound of formula I is prepared where A2 is 2-aminopyridyl,
R15 is tert-butyloxycarbonyl,
Y is —$(C_3$-$C_8)$-cycloalkyl, which is unsubstituted or substituted by one or two methyl and
Z is —$(C_1$-$C_4)$-alkyl.

4. A process for obtaining a compound of formula II:

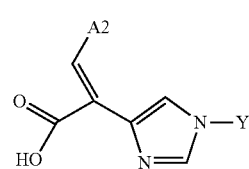
(II)

which comprises

C) reacting a compound of the formula I:

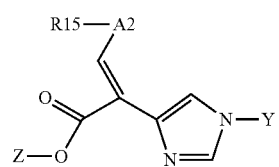
(I)

wherein

A2 is aminopyridyl, in which aminopyridyl is unsubstituted or substituted independently of one another once, twice or three times by halogen or methyl, Y is —$(C_3$-$C_8)$-cycloalkyl, in which cycloalkyl is unsubstituted or substituted independently of one another once, twice or three times by R1, where R1 is
a) phenyl, where phenyl is unsubstituted or substituted once, twice or three times independently of one another by —$(C_1$-$C_4)$ alkyl,
b) halogen,
c) —$(C_1$-$C_4)$-alkyl,
d) —$(C_3$-$C_6)$-cycloalkyl,
e) —$CF_3$,
f) —O—$CF_3$,
g) triazolyl or
h) pyridinyl, R15 is an amino protecting group, and Z is 1) —$(C_1$-$C_6)$-alkyl,
2) —$(C_1$-$C_6)$-alkyl-OH,
3) —$(C_1$-$C_4)$-alkylene-$(C_3$-$C_6)$-cycloalkyl,
4) —$CH_2$-phenyl, wherein phenyl is unsubstituted or substituted once or twice by $NO_2$ or methoxy,
5) —$CH_2$—CH=$CH_2$ or
6) —$(C_1$-$C_{10})$-alkylene-O—C(O)—O—$(C_3$-$C_6)$-cycloalkyl, with an acid to give a compound of formula II, and D) optionally, when the compound of the formula II which has been prepared by process step C) is in enantiomeric forms, fractionating by salt formation with enantiopure acids or bases; performing chromatography on chiral stationary phases; or derivatizating using chiral enantiopure compounds, separating the diastereomers obtained in this way, and eliminating the chiral auxiliary groups into the pure enantiomers.

5. The process as claimed in claim 4, wherein the compound of formula II is prepared where A2 is aminopyridyl, in which aminopyridyl is unsubstituted or substituted independently of one another once, twice or three times by halogen or methyl;

Y is —$(C_3$-$C_8)$-cycloalkyl, in which cycloalkyl is unsubstituted or substituted independently of one another once, twice or three times by R1, where R1 is
a) phenyl, where phenyl is unsubstituted or substituted once, twice or three times independently of one another by —($C_1$-$C_4$) alkyl,
b) halogen,
c) —($C_1$-$C_4$)-alkyl,
d) —($C_3$-$C_6$)-cycloalkyl,
e) —$CF_3$,
f) —O—$CF_3$,
g) triazolyl or
h) pyridinyl;

R15 is an amino protecting group selected from tert-butyloxycarbonyl, benzyloxycarbonyl, p-methoxybenzylcarbonyl, N-formyl, N-acetyl, N-benzyl, N-1-(diphenyl)methyl, N-trityl, (4-methoxyphenyl) diphenylmethyl, N-dialkyl phosphoramidates and N-p-toluenesulfonyl; and Z is 1) —($C_1$-$C_6$)-alkyl,
2) —($C_1$-$C_6$)-alkyl-OH,
3) —($C_1$-$C_4$)-alkylene-($C_3$-$C_6$)-cycloalkyl or
4) —($C_1$-$C_{10}$)-alkylene-O—C(O)—O—($C_3$-$C_6$)-cycloalkyl.

6. The process as claimed in claim 4, wherein the compound of formula II is prepared where
A2 is 2-aminopyridyl,
R15 is tert-butyloxycarbonyl,
Y is —($C_3$-$C_8$)-cycloalkyl, which is unsubstituted or substituted by one or two methyl and
Z is —($C_1$-$C_4$)-alkyl.

7. The process as claimed in claim 4, where the acid is selected from the group consisting of mineral acids selected from HBr, HCl, HI, $H_2SO_4$, and $H_3PO_4$, and organic acids selected from acetic acid, trifluoromethane sulfonic acid and trifluoroacetic acid.

8. A process for obtaining a compound of formula V:

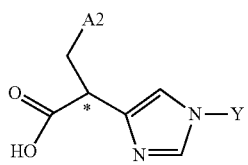

(V)

wherein
A2 is aminopyridyl, in which aminopyridyl is unsubstituted or substituted independently of one another once, twice or three times by halogen or methyl;
Y is —($C_3$-$C_8$)-cycloalkyl, in which cycloalkyl is unsubstituted or substituted independently of one another once, twice or three times by R1,
where R1 is
a) phenyl, where phenyl is unsubstituted or substituted once, twice or three times independently of one another by —($C_1$-$C_4$) alkyl,
b) halogen,
c) —($C_1$-$C_4$)-alkyl,
d) —($C_3$-$C_6$)-cycloalkyl,
e) —$CF_3$,
f) —O—$CF_3$,
g) triazolyl or
h) pyridinyl;

which process comprises
E) reacting a compound of the formula IV:

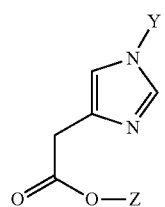

(IV)

wherein
Z is 1) —($C_1$-$C_6$)-alkyl,
2) —($C_1$-$C_6$)-alkyl-OH,
3) —($C_1$-$C_4$)-alkylene-($C_3$-$C_6$)-cycloalkyl,
4) —$CH_2$-phenyl, wherein phenyl is unsubstituted or substituted once or twice by $NO_2$ or methoxy,
5) —$CH_2$—CH=$CH_2$ or
6) —($C_1$-$C_{10}$)-alkylene-O—C(O)—O—($C_3$-$C_6$)-cycloalkyl,
and Y is as defined above,
with the compound of formula VII

R15-A2-CHO (VII)

wherein R15 is an amino-protecting group and A2 is as defined above, to give a compound of formula I:

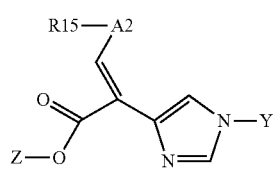

(I)

F) reacting a compound of the formula I with an acid to give a compound of formula II:

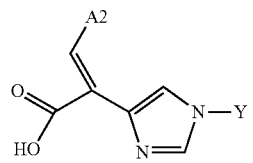

(II)

G) and hydrogenating a compound of the formula II, wherein the compound of formula II may be present in the E or in the Z configuration on the double bond,
in the presence of hydrogen and a catalyst to give a compound of formula V, wherein the compound of formula V is present either as the R- or S-enantiomer or as an enantiomer mixture in which one enantiomer is enriched compared to the other.

* * * * *